United States Patent
Koob

(10) Patent No.: US 10,617,785 B2
(45) Date of Patent: Apr. 14, 2020

(54) COLLAGEN REINFORCED TISSUE GRAFTS

(71) Applicant: MiMedx Group, Inc., Marietta, GA (US)

(72) Inventor: Thomas J. Koob, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 14/838,305

(22) Filed: Aug. 27, 2015

(65) Prior Publication Data

US 2016/0199537 A1   Jul. 14, 2016

Related U.S. Application Data

(60) Provisional application No. 62/043,300, filed on Aug. 28, 2014.

(51) Int. Cl.
| | | |
|---|---|---|
| A61L 15/40 | (2006.01) | |
| A61L 27/54 | (2006.01) | |
| A61L 31/04 | (2006.01) | |
| A61L 27/36 | (2006.01) | |
| A61L 15/32 | (2006.01) | |
| A61L 27/24 | (2006.01) | |

(52) U.S. Cl.
CPC ............ *A61L 15/40* (2013.01); *A61L 15/325* (2013.01); *A61L 27/24* (2013.01); *A61L 27/3604* (2013.01); *A61L 27/3645* (2013.01); *A61L 27/3675* (2013.01); *A61L 27/54* (2013.01); *A61L 31/044* (2013.01); *A61L 2430/32* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 3,272,204 A | 9/1966 | Artandi | |
| 4,060,081 A * | 11/1977 | Yannas | A61F 2/105 128/DIG. 8 |
| 4,642,117 A * | 2/1987 | Nguyen | A61L 27/24 128/DIG. 8 |
| 4,703,108 A | 10/1987 | Silver et al. | |
| 4,847,049 A | 7/1989 | Yamamoto | |
| 5,118,867 A | 6/1992 | Bahrmann et al. | |
| 5,284,655 A | 2/1994 | Bogdansky et al. | |
| 5,294,314 A * | 3/1994 | Nesburn | A61L 24/102 128/DIG. 8 |
| 5,412,076 A * | 5/1995 | Gagnieu | A61L 15/325 106/150.3 |
| 5,541,232 A | 7/1996 | Howell et al. | |
| 6,030,635 A | 2/2000 | Gertzman et al. | |
| 6,165,489 A * | 12/2000 | Berg | A61L 26/0033 424/423 |
| 6,387,369 B1 | 5/2002 | Pittenger et al. | |
| 6,565,960 B2 | 5/2003 | Koob et al. | |
| 6,821,530 B2 | 11/2004 | Koob et al. | |
| 6,936,271 B1 | 8/2005 | Oliver et al. | |
| 7,101,857 B2 | 9/2006 | Sung et al. | |
| 7,311,904 B2 | 12/2007 | Hariri | |
| 7,311,905 B2 | 12/2007 | Hariri | |
| 7,901,455 B2 | 3/2011 | Koob et al. | |
| 8,067,044 B2 | 11/2011 | Henry et al. | |
| 8,153,162 B2 | 4/2012 | Tseng et al. | |
| 8,177,839 B2 | 5/2012 | Koob et al. | |
| 8,192,481 B2 | 6/2012 | King | |
| 8,231,908 B2 | 7/2012 | Kinoshita et al. | |
| 8,323,701 B2 | 12/2012 | Daniel et al. | |
| 8,357,403 B2 | 1/2013 | Daniel et al. | |
| 8,623,421 B2 | 1/2014 | Daniel | |
| 8,904,664 B2 | 12/2014 | Pringle et al. | |
| 8,961,617 B2 | 2/2015 | Young | |
| 9,155,799 B2 | 10/2015 | Koob | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2004/0028711 A1 | 2/2004 | Uchida et al. | |
| 2004/0048796 A1 | 3/2004 | Hariri et al. | |
| 2004/0082063 A1 * | 4/2004 | Deshpande | C12N 5/0062 435/366 |
| 2005/0107876 A1 | 5/2005 | Kim et al. | |
| 2006/0140913 A1 | 6/2006 | Bhatia | |
| 2006/0166361 A1 | 7/2006 | Seyda et al. | |

(Continued)

FOREIGN PATENT DOCUMENTS

| | | |
|---|---|---|
| CN | 101433556 | 5/2009 |
| EP | 0 431 164 A1 | 6/1991 |

(Continued)

OTHER PUBLICATIONS

Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Borkow et al., "Reducing the risk of skin pathologies in diabetics by using copper impregnated socks", Medical Hypotheses, 2009, 1-4, doi:10.1016/j.mehy.2009.02.050.
Database WPI XP002732611 & KR 2001-0100588, dated Nov. 14, 2001-Abstract.
EpiFix Product Brochure (2011).
Extended European Search Report for European Application No. 13830009.0 dated Feb. 25, 2016, 9 pages.
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
http://proxybiomedical.com/Images/ML005-01-Rev002.pdf (accessed on Jun. 5, 2014.).

(Continued)

*Primary Examiner* — Blaine Lankford
(74) *Attorney, Agent, or Firm* — Alston & Bird LLP

(57) ABSTRACT

This invention is directed to a multi-layered tissue graft comprising a collagen layer and at least one separated and washed placental tissue component and/or umbilical cord component, wherein the collagen is human collagen substantially free of non-human antigens.

9 Claims, No Drawings

(56) References Cited

U.S. PATENT DOCUMENTS

| | | |
|---|---|---|
| 2006/0210532 A1 | 9/2006 | Carmeliet et al. |
| 2007/0020225 A1 | 1/2007 | Abramson et al. |
| 2007/0021762 A1 | 1/2007 | Liu et al. |
| 2007/0071740 A1 | 3/2007 | Tseng et al. |
| 2007/0071828 A1 | 3/2007 | Tseng et al. |
| 2007/0148138 A1* | 6/2007 | Barrows ............ A61K 35/36 424/93.7 |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0050347 A1 | 2/2008 | Ichim |
| 2008/0069895 A1 | 3/2008 | Liu et al. |
| 2008/0131966 A1 | 6/2008 | Hariri |
| 2008/0181967 A1 | 7/2008 | Liu et al. |
| 2008/0233552 A1 | 9/2008 | Ma et al. |
| 2009/0012629 A1 | 1/2009 | Yao et al. |
| 2009/0036996 A1 | 2/2009 | Roeber |
| 2009/0053290 A1 | 2/2009 | Sand et al. |
| 2009/0092664 A1 | 4/2009 | Mumper et al. |
| 2009/0142831 A1 | 6/2009 | Hariri |
| 2009/0287308 A1 | 11/2009 | Davis et al. |
| 2009/0291891 A1 | 11/2009 | Neufeld |
| 2010/0028849 A1 | 2/2010 | Shelby et al. |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Livesey et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0307059 A1 | 12/2011 | Young et al. |
| 2012/0010708 A1 | 1/2012 | Young et al. |
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0018463 A1* | 1/2013 | Haddad ............... A61F 2/08 623/13.12 |
| 2013/0230561 A1 | 9/2013 | Daniel et al. |
| 2013/0244943 A1* | 9/2013 | Yu ..................... A61L 27/24 514/17.2 |
| 2013/0344162 A1 | 12/2013 | Morse et al. |
| 2014/0067058 A1 | 3/2014 | Koob et al. |
| 2014/0142025 A1 | 5/2014 | Koob |
| 2014/0142041 A1 | 5/2014 | Koob |
| 2014/0205646 A1 | 7/2014 | Morse et al. |
| 2014/0308233 A1 | 10/2014 | Koob |
| 2014/0356451 A1 | 12/2014 | Koob |

FOREIGN PATENT DOCUMENTS

| | | |
|---|---|---|
| EP | 0 431 479 A1 | 6/1991 |
| EP | 0 637 452 | 2/1995 |
| EP | 0 506 207 B1 | 11/1999 |
| JP | H09225018 A | 9/1997 |
| JP | 2006507851 A | 3/2006 |
| JP | 2009539378 A | 11/2009 |
| KR | 10199111272 | 8/1991 |
| KR | 2001/100588 | 11/2001 |
| WO | WO-87/00062 A1 | 1/1987 |
| WO | WO-88/03805 A1 | 6/1988 |
| WO | WO-01/08716 A1 | 2/2001 |
| WO | WO-2004/026244 A2 | 4/2004 |
| WO | WO-2005/017165 | 2/2005 |
| WO | WO-2007/010305 | 1/2007 |
| WO | WO-2007/076522 | 7/2007 |
| WO | WO-2007/083984 A1 | 7/2007 |
| WO | WO-2009/033160 A1 | 3/2009 |
| WO | WO-2009/048908 | 4/2009 |
| WO | WO-2009/132186 A1 | 10/2009 |
| WO | WO-2010/029344 A2 | 3/2010 |
| WO | WO-2011/103470 | 8/2011 |
| WO | WO-2012/003377 | 1/2012 |
| WO | WO-2012/069559 A1 | 5/2012 |
| WO | WO-2012/112410 A2 | 8/2012 |
| WO | WO-2012/112417 A2 | 8/2012 |
| WO | WO-2013/095830 A1 | 6/2013 |
| WO | WO-2014/028327 A1 | 2/2014 |

OTHER PUBLICATIONS

Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.

Koob et al., "Biological properties of dehydrated human amnion/chorion composite graft: implications for chronic wound healing," International Wound Journal, (2013), 10(5):493-500.

Mayfield et al., "Watertight closure of spinal dura mater: Technical note," J. Neurosurg., (1975), 43(5):639-640.

MiMedx Group Announces Launch of EpiFixTM and Hiring of Vice President, Wound Care, Mimedx Press Release (2011).

MiMedx Press Release, "MiMedx Scientific Study is Electronically Published in the International Wound Journal", 2013.

Nagaya et al., "Transplantation of mesenchymal stem cells improves cardiac function in a rat model of dilated cardiomyopathy", Circulation, 2005, 112(8):1128-1135.

Parolini et al., 'Toward cell therapy using placenta-derived cells: disease mechanisms, cell biology, preclinical studies, and regulatory aspects at the round table', Stem Cells and Development, 2010, vol. 19, No. 2, pp. 143-154.

PCT International Preliminary Report on Patentability for International Patent Application No. PCT/US2013/055003 dated Nov. 27, 2014. 28 pages.

PCT International Search Report and Written Opinion for PCT Patent Application No. PCT/US2013/055003 dated Nov. 19, 2013. 12 pages.

PCT International Search Report and Written Opinion for International Patent Application No. PCT/US2015/047303 dated Nov. 26, 2015. 13 pages.

PCT International Search Report and Written Opinion for PCT Patent Application No. PCT/US2013/064146 dated Jan. 9, 2014. 9 pages.

Toda et al., "The potential of amniotic membrane/amnion-derived cells for regeneration of various tissues." Journal of Pharmacological Sciences, 2007, 105:215-228.

Koob, T., et al., "Material properties of polymerized NDGA-collagen composite fibers: development of biologically based tendon constructs," Biomaterials, 23(1):2013-212 (2002).

Office Action for Japanese Patent Application No. 2017-511721 dated May 7, 2019.

Office Action for European Application No. 15774739.5 dated Oct. 2, 2018.

\* cited by examiner

COLLAGEN REINFORCED TISSUE GRAFTS

CROSS-REFERENCE TO RELATED APPLICATIONS

This application claims the benefit of U.S. provisional patent application No. 62/043,300, filed on Aug. 28, 2014. The content of the prior application is incorporated herein by reference in its entirety.

FIELD OF THE INVENTION

The invention relates to laminated tissue grafts comprising collagen and placental tissue and/or umbilical cord components and associated methods.

BACKGROUND OF THE INVENTION

Human placental tissue components (e.g. amniotic membranes) have been used for various types of reconstructive surgical procedures since the early 1900s. Typically, the placental tissue is harvested after an elective Cesarean surgery. The placental tissue components include the placenta and amniotic sac. The umbilical cord is also associated with the placenta. The amniotic sac, commonly referred to as the amniotic membrane, has two primary layers of tissue, amnion and chorion. Amnion tissue is the innermost layer of the amniotic sac and in direct contact with the amniotic fluid. The amniotic sac contains the amniotic fluid and protects the fetal environment. The membrane layers of the amnion include a single layer of epithelium cells, thin reticular fibers (basement membrane), a thick compact layer, and a fibroblast layer.

A limitation of existing placental tissue grafts is that they generally do not have sufficient tensile strength, stiffness and/or resistance to sheer for some medical applications where they would otherwise be beneficial. Additives to tissue grafts that confer strength, however, can induce an unwanted immune response in the subject. Consequently, placental tissue grafts are needed with increased strength and resistance to tearing, but that do not illicit an unwanted immune response in the subject.

SUMMARY OF THE INVENTION

This invention is directed to multi-layer tissue grafts comprising at least one collagen layer and at least one layer derived from placental components and/or at least one layer derived from umbilical cord components, and methods of making and using the same. These tissue grafts have numerous medical applications, for example in wound healing, surgical procedures, prevention of scarring or adhesions, dental applications, etc. Conventional placental tissue grafts generally have inadequate tensile strength and stiffness for many surgical applications, particularly after wetting the grafts with saline or blood. Tissue grafts that include additives to promote stiffness are often immunogenic and can initiate an unwanted inflammatory response in the patient.

This invention is predicated on the discovery that adding layers of human collagen, derived from immune-privileged tissue, to layers of placental tissue (e.g., such as amnion) and/or layers of umbilical cord components creates a tissue graft with higher tensile strength and resistance to sheer than the placental tissue alone. As such, the disclosed collagen-containing multi-layer tissue grafts have important advantages over conventional multi-layer tissue grafts. The collagen-containing multi-layer tissue grafts exhibit high tensile strength and toughness; they are non-fragile and exhibit sufficient sturdiness to enable them to be readily handled during medical applications, e.g., implantation surgery, with reduced risk of damage or disintegration. The collagen-containing multi-layer tissue grafts are stiff and rigid. They can be formed by folding or bending to a desired configuration to fit a surgical site and retain that configuration. Further, the collagen layers within the multi-layered grafts can be "tuned" with more or less collagen to adjust the mechanical properties of the multi-layer tissue grafts.

Because the collagen derives from immune-privileged human tissue, the disclosed tissue grafts do not illicit an unwanted immune response in the subject that would require medical treatment for the immune response. By contrast, reconstituted collagen from human cadaveric donors, i.e., allografts, and nonhuman species, termed xenografts, present a greater challenge for in vivo use with respect to antigenicity and induction of a foreign body response.

In one aspect, this invention relates to a multi-layered tissue graft comprising a collagen layer and at least one separated and washed placental tissue component and/or an umbilical cord component, where the collagen is human collagen substantially free of non-human antigens. The placental tissue component generally derives from an amniotic sac. The umbilical cord component generally includes Wharton's jelly. The collagen of the collagen layer derives from immune-privileged tissue such as a placental tissue component.

In another aspect, this invention relates to a composition comprising any of the multi-layered tissue grafts disclosed herein, wherein the tissue graft has been dehydrated to have a water content of less than 20 wt. % and micronized to a size, i.e., width, of less than about 10 μm.

In another aspect, this invention relates to a method for treating a subject, the method comprising contacting the subject with a multi-layered tissue graft as described herein.

DETAILED DESCRIPTION OF THE INVENTION

As noted above, this invention is directed, in part, to multi-layer tissue grafts comprising placental components and collagen. However, prior to discussing this invention in further detail, the following terms will be defined.

Definitions

As used herein, the following terms have the following meanings.

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

The term "subject" as used herein is any vertebrate organism including but not limited to mammalian subjects such as humans, farm animals, domesticated pets and the like.

The term "biocompatible" as used herein refers to a material that is suitable for implantation or injection into a subject. In various aspects, a biocompatible material does not cause toxic or injurious effects once implanted in the subject.

The term "amnion" as used herein includes amniotic membrane where the intermediate tissue layer is intact or has been substantially removed.

The term "placental tissue" refers to any and all of the well-known components of the placenta including but not limited to amnion, chorion, and the like, and including processed tissue, such as dehydrated placental tissue and micronized placental tissue. The term "placental tissue" as used herein does not include any of the umbilical cord components (e.g., Wharton's jelly, umbilical cord vein and artery, and surrounding membrane).

"Collagen," as used herein, refers to biocompatible collagen derived from immune-privileged human tissue, such as placental tissue or an umbilical cord. The collagen, once obtained from human immune-privileged human tissue, may be in any form, such as a gel, gelatin, fibril, slurry, hydrogel or a film. It should be noted that the fibrous layer of amnion (i.e., the basement membrane) contains collagen types IV, V, and VII. The collagen layers described herein are separate and apart from the collagen, if any, that exists in the other layers, such as amnion layers, of the disclosed multi-layer tissue grafts. In some aspects, the collagen is free or substantially free of other components, including elastin, fibronectin, and/or laminin.

"Substantially free of other components" as used herein means that the collagen is at least about 90% pure collagen, preferably at least about 95% pure, more preferably at least about 97% pure, and even more preferably more than 97% pure (e.g., more than 98%, more than 99%, or 100% pure). In a preferred embodiment, the collagen does not contain any growth factors or other bioactive factors.

The term "non-human antigen" refers to any agent (e.g., protein, peptide, polysaccharide, glycoprotein, glycolipid, nucleic acid, or combination thereof) of non-human origin that, when introduced into a human, is immunogenic, eliciting an unwanted immune response that requires medical treatment for the manifestations (e.g., inflammation, etc.) of the immune response. As defined herein, the non-human antigen-induced immune response can be humoral or cell-mediated, or both.

"Biocompatible" as used herein refers to the property of being biologically compatible by not producing a toxic, injurious, or immunological response or rejection in living tissue that, for example, would cause a subject to be medically treated for the immunological response.

The term "dehydrated" when defining a substance, such as micronized Wharton's jelly, amnion, chorion, etc., means that the substance has a water content of no more than 10%, no more than 5%, no more than 1%, no more than 0.5%, amnion, no more than 0.2%, no more than 0.1%, or no more than 0.01%, or is free of any water. The term "dehydrate" or "dry", or grammatical equivalent means to remove water substantially (e.g., to remove at least 90%, 95%, 99%, 99.5%, 99.8%, 99.9% or 99.99% of the water content in the substance) or completely from a substance to produce the dehydrated substance.

When referring to values or ranges, it should be understood that any subvalue or subrange from within the values described, including endpoints, are contemplated for use with the embodiments described herein.

In one aspect of this invention, a multi-layered tissue graft is provided, comprising a collagen layer and at least one separated and washed placental tissue component and/or at least one layer derived from umbilical cord components, wherein the collagen is human collagen substantially free of non-human antigens. Described below is each of the components of the multi-layered tissue graft, as well as the multi-layered tissue graft that results by combining these components, and micronized compositions made from the same.

The Reconstituted Collagen Layers

One component of the multi-layered tissue graft includes a collagen layer that derives from human collagen substantially free of non-human antigens. Generally, the collagen layers derive from collagen that has been reconstituted from human placental components, according to known protocols. Human placenta is used as a source for the collagen to minimize immunogenic reactions and to reduce host-mediated breakdown. Once obtained from human placenta, the reconstituted collagen is incorporated into the multi-layered tissue grafts described herein.

In certain embodiments, the reconstituted collagen is prepared from human placenta according to the methods described herein or from known methods.

Collagen molecules consist of a triple helix of three polypeptide chains (a-chains) with short, flanking, nonhelical telopeptides. These molecules spontaneously assemble into fibrils. Following incorporation into the fibril, covalent, intermolecular, lysine-derived crosslinks form between the telopeptides and helical domains of neighboring molecules. The cross-linked fibril is the fundamental unit of mature collagen fiber systems within all connective tissues.

Intact native collagen molecules containing the telopeptides can be obtained from tissues by acid and enzyme extraction. The triple helical domain of the native collagen molecule is obtained from connective tissues by enzymatic, e.g., pepsin, treatment in acid. Pepsin cleaves in the telopeptide region of the molecule inside the cross-linking domain but outside the helical domain, thereby liberating the molecule.

The acid-extracted and pepsin-solubilized collagen can be purified by salt fractionation in acetic acid. The major fibrillar collagens precipitate and are collected by centrifugation. The collagen can be redissolved in acetic acid and precipitated a second time. The precipitate is redissolved in acetic acid and residual salt is removed by dialysis. The purity of the collagen preparation can be assessed by polyacrylamide gel electrophoresis and amino acid analysis.

Both intact and pepsin-solubilized collagen molecules spontaneously form fibrils in vitro at neutral pH at 37° C. These fibrils resemble native fibrils as found in vivo. The purified collagen molecules dissolved in acid are neutralized, generally by dialysis, into phosphate buffered saline. The molecules are soluble at neutral pH at 4° C. To form fibrils, the temperature of the collagen solution is increased to 37° C.

The collagen fibrils can be sterilized according to techniques known to those of skill in the art for sterilizing such compositions. In certain embodiments, the collagen is filtered through appropriate filters to yield sterilized collagen followed by treatment under aseptic conditions. Useful filters include 0.22 μm and 0.1 μm filters, and other filters recognized by those of skill for sterilization. Further, in certain embodiments the collagen is filtered to remove viruses and/or endotoxins.

The initial collagen solution is generally a viscous liquid that can be easily loaded into molds or layers to form collagen that can be incorporated as sheets into the multi-layer grafts described herein. The viscous collagen liquid gradually transforms into a loose gel. The rigidity of the collagen can be strengthened by crosslinking i.e., fixing, the collagen within the solution before it forms a gel.

Thus, in some embodiments, and as discussed in greater detail below, the collagen layer is fixed (i.e., crosslinked) to increase its strength before it is incorporated into the multi-layer tissue grafts. Any suitable crosslinking agent may be used. Non-limiting crosslinking agents include nordihydroguaiaretic acid (NDGA), 3,4-dyhydroxyphenylalanine, dopamine, 3,4-dihydroxybenzaldehyde, 3,4-dihydroxybenzoic acid, a carbodiimide, glutaraldehyde or another di- or multi aldehyde, formaldehyde, tannic acid, isocyanates, pluronics, and epoxy resins. In another embodiment, the cross-linking agent is NDGA. See, for example, Koob and Hernandez, *Material properties of polymerized NDGA-collagen composite fibers: development of biologically based tendon constructs*, Biomaterials 2002 January; 23 (1): 203-12; U.S. Pat. No. 6,565,960, and U.S. patent application Ser. No. 13/815,736, the contents of which are hereby incorporated by reference as if recited in full herein.

As noted, the collagen from the collagen solution is optionally crosslinked and can be dried into a gel, hydrogel, gelatin, slurry, film, fibers, sheets, layers or other form of collagen. Non-limiting examples of forms of collagen that can be used in the present technology can be found, for example, in U.S. patent application Ser. No. 13/815,736, which is incorporated herein by reference in its entirety. The collagen (e.g., fibers, sheets or layers) can also include non-collagenous components or biocompatible materials or drugs that facilitate tissue growth or other desired effects. See, U.S. Pat. No. 6,821,530, incorporated herein by reference.

In some embodiments, the multi-layered tissue graft includes collagen having a tensile strength of at least about 250, 500, 600, 700, 800, 900, or 1000 kilopascals (kPa) or 10, 20, 30, 40, 50, 75, 100 or 200 megapascals (MPa). In a preferred embodiment, the collagen has a tensile strength of about 500 kPa to about 10 MPa. In some embodiments, the multi-layered tissue graft includes collagen having a stiffness of at least about 50, 75, 100, 200, 300, 400 or 500 MPa. In a preferred embodiment, the collagen has a stiffness of about 100 MPa to about 500 MPa. The tensile strength and stiffness may be calculated according to known methods such as those described in T. Koob, Biomaterials 2002 January; 23 (1): 203-12. For example, the tensile strength and stiffness may be calculated from collagen fibrils of about 2 cm long that have been hydrated throughout. In some embodiments, the collagen is cross-linked. Crosslinking of collagen results in a 2-fold to 20-fold increase in tensile strength. In one embodiment, the tissue graft includes cross-linked collagen with a tensile strength of about 1 MPa to about 200 MPa. It should be understood that any subvalue or subrange from within the values described above, including endpoints, are contemplated for use with the embodiments described herein.

In some embodiments, the multi-layered tissue graft includes from 1 to 10 weight percent (wt %), 10 to 20 wt %, 20 to 30 wt %, 30 to 40 wt %, 40 to 50 wt %, 50 to 60 wt %, 60 to 70 wt %, 70 to 80 wt % collagen relative to the total weight of the multi-layered tissue graft. It should be understood that any subvalue or subrange from within the values described above, including endpoints, are contemplated for use with the embodiments described herein.

Layers Derived from the Placental Components

Another component of the multi-layered tissue graft includes the one or more placental tissue components. The placental tissue components include the umbilical cord, placenta, and amniotic sac. The layers of the multi-layered tissue graft may be laminated together according to known methods, such as those described in PCT Application Nos. PCT/US12/24798 and PCT/US13/54322 (WO2014/028327), and U.S. provisional Application Ser. Nos. 61/442,346, 61/543,995, and 61/683,700; U.S. Patent Publication No. 2013-0344162. The contents of these applications are specifically incorporated by reference in their entireties.

In one embodiment, the multi-layered tissue graft includes one or more layers derived from placental tissue components and one or more collagen layers, where the placental tissue component derives from an amniotic sac. The amniotic sac (i.e., amniotic membrane) contains amniotic fluid and protects the fetal environment. The amniotic sac includes two primary layers of tissue, amnion and chorion. Amnion tissue is the innermost layer of the amniotic sac and in direct contact with the amniotic fluid. The membrane layers of the amnion consist of a single layer of epithelial cells, thin reticular fibers (basement membrane), a thick compact layer, and a fibroblast layer.

Amnion and chorion layers of the placenta tissue can be carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion layer can be separated from the chorion layer. The amnion appears as a thin, opaque layer on the chorion.

In one embodiment of the multi-layered tissue graft, at least one amnion layer comprises an epithelial side and a fibroblast cellular side. In some embodiments, the epithelial side is retained in an amnion layer of a multi-layered graft that is intended for topical use. For example, a multi-layered graft having an amnion layer with an epithelial side can be used to treat surface burns of human skin because the epithelial side provides a protective barrier similar to the epithelial layer in skin. Alternatively, a multi-layered graft having an amnion layer without an epithelial side, that is the epithelial cells have been substantially or fully removed, can be used internally in a patient. For example, a multi-layered graft having an amnion layer without an epithelial side can be used by a surgeon to fill or patch an internal incision, where a protective epithelial barrier is not needed. Thus, in some embodiments, the multi-layered tissue grafts include an amnion layer that retains all or substantially all of its epithelial cells. In some embodiments, the multi-layered tissue grafts include an amnion layer that has all or substantially all of its epithelial cells removed i.e., decellularized.

As noted, the amnion layer also includes a fibroblast cellular side that may be retained or removed in the multi-layered tissue grafts. The fibroblast layer can be identified by gently contacting each side of the amnion layer with, for example, a piece of sterile gauze or a cotton tipped applicator. The fibroblast layer will stick to the test material. Thus, in some embodiments, the fibroblast layer can act as a glue of sorts to bind the amnion to other layers of the multi-layer tissue graft, such as a collagen layer, chorion layer or an umbilical cord layer. Also, without being bound by theory, it is believed that the fibroblast layer contains growth factors that promote healing and/or recruit stem cells. Thus, in some embodiments, the multi-layered tissue grafts include an amnion layer that retains all or substantially all of its fibroblast layer. In some embodiments, the multi-layered tissue grafts include an amnion layer that has all or substantially all of its fibroblast layer removed, i.e., decellularized.

Thus, either side of each amnion layer can be partially or substantially "decellularized," meaning that the epithelial and/or fibroblast cells on either side have been partially or substantially removed. The term "substantially removed or decellularized" with respect to the amount of fibroblast or epithelium removed is defined herein as removing greater than 90%, greater than 95%, or greater than 99% of the epithelial or fibroblast cells from the amnion. The term "partially removed or decellularized" with respect to the amount of fibroblast or epithelium removed is defined herein as removing between 20% and 70%, and preferably between 30% and 65%, of the epithelial or fibroblast cells from the amnion. Decellularization generally involves the physical and/or chemical removal of cells present in the amnion, which includes epithelial cells and fibroblast cells. Despite decellularization, epithelial cells and/or fibroblast cells may optionally remain on the membrane. Complete removal of the fibroblast reduces the ability of the tissue graft to release components such as proteins and growth factors which play a critical role in wound healing.

Partial removal of the epithelial cells from the amnion membrane may result in an uneven topography of the epithelial cell layer. Partial removal of the epithelial cells from the amnion membrane may result in increased surface area of the epithelial cell layer. Without being bound by theory, it is believed that the removal of only a portion of the epithelial cell layer results in slower diffusion of bioactive factors from the areas of the epithelial cell surface that retain epithelial cells, and faster diffusion from and/or better host access to the areas where the basement membrane is exposed by partial removal of the epithelial cells.

The epithelial cellular layer can be removed by a variety of techniques. For example, the epithelial cellular layer can be scraped off of the amnion using a cell scraper. Other techniques include, but are not limited to, freezing the membrane, physical removal using a cell scraper, or exposing the epithelial cells to nonionic detergents, anionic detergents, and nucleases. If partial removal of the epithelial cellular layer is desired, the membrane can be exposed to the above conditions at lower concentrations and/or for shorter periods of time than those used to fully de-epithelialize the amnion.

The presence or absence of epithelial cells remaining on the amnion layer, and/or determination that the basement membrane remains intact, can be evaluated using techniques known in the art. For example, after partial removal of the epithelial cell layer, a representative tissue sample from the processing lot is placed onto a standard microscope examination slide. The tissue sample is stained using Eosin Y Stain. The sample is then covered and allowed to stand. Once an adequate amount of time has passed to allow for staining, visual observation is done under magnification. Cellular material will stain dark, indicating the presence of cells.

In some embodiments of the multi-layer tissue grafts, the at least one amnion layer may comprise an epithelial side and a fibroblast side, wherein neither side has been partially or substantially decellularized. In other embodiments of the multi-layer tissue grafts, the at least one amnion layer may comprise an epithelial side and a fibroblast side, wherein the epithelial side has been partially or substantially decellularized, but the fibroblast side has not been partially or substantially decellularized. In still other embodiments of the multi-layer tissue grafts, the at least one amnion layer may comprise an epithelial side and a fibroblast side, wherein both the epithelial side and the fibroblast side have been partially or substantially decellularized.

In some embodiments, the multi-layered tissue graft includes from 1 to 10 wt %, 10 to 20 wt %, 20 to 30 wt %, 30 to 40 wt %, 40 to 50 wt %, 50 to 60 wt %, 60 to 70 wt %, 70 to 80 wt % amnion relative to the total weight of the multi-layered tissue graft. It should be understood that any subvalue or subrange from within the values described above, including endpoints, are contemplated for use with the embodiments described herein.

In the case when a chorion layer is added to the tissue graft, the following exemplary procedure can be used. After separation of the chorion from the amnion and removal of clotted blood from the fibrous layer, the chorion is rinsed in 18% saline solution for 30 min. During the first rinse cycle, 18% saline is heated in a sterile container using laboratory heating plate such that the solution temperature is approximately 48° C. The solution is decanted, the chorion tissue is placed into the sterile container, and decanted saline solution is poured into the container. The container is sealed and placed on rocker plate and agitated for 1 hour. After 1 hour agitation bath, the tissue is removed and placed into a second heated agitation bath for an additional 1 hour rinse cycle. Next, the chorion tissue is placed into 200 ml of 0.5% Triton-X wash solution. The container is sealed and agitated without heat for 2 hours. The tissue is next washed with deionized water (four washes of 250 ml of DI water per wash) with vigorous motion for each rinse. The tissue is removed and placed into a container of 1×PBS w/EDTA solution. The container is sealed and agitated for 1 hour at controlled temperature for 8 hours. The tissue is removed and rinsed using sterile water. A visual inspection is performed to remove any remaining discolored fibrous blood material from the membrane. The membrane should have a cream white visual appearance with no evidence of brownish discoloration.

In some embodiments, the multi-layered tissue graft includes from 1 to 10 wt %, 10 to 20 wt %, 20 to 30 wt %, 30 to 40 wt %, 40 to 50 wt %, 50 to 60 wt %, 60 to 70 wt %, 70 to 80 wt % chorion relative to the total weight of the multi-layered tissue graft.

Layers Derived from Umbilical Cord Components

In some embodiments, the multi-layered tissue graft includes one or more layers derived from one or more collagen layers and one or more layers derived from umbilical cord components. The umbilical cord is a substantially tubular organ, typically 10-15 cm in length, that connects the fetus to the placenta and houses the umbilical vessels. The umbilical cord includes an outer membrane that wraps around two umbilical arteries and one umbilical vein, which are contained within a ground substance known as Wharton's jelly. The main components of Wharton's jelly are proteoglycans. Wharton's jelly also contains large, stellate fibroblasts and macrophages.

The umbilical cord or components thereof may include the umbilical cord membrane, but can also include Wharton's jelly and/or one or more of the umbilical vessels. In one embodiment, the umbilical cord or components thereof is an umbilical cord membrane substantially isolated from the remaining umbilical cord components (e.g., Wharton's jelly and umbilical vessels). In another embodiment, the umbilical cord or components thereof includes an umbilical cord membrane and Wharton's jelly (that is, the ground material in which the umbilical cord vessels are contained in the intact umbilical cord) that are isolated from the remaining umbilical cord components (e.g., umbilical cord vessels). In another specific embodiment, the umbilical cord or components thereof includes the membrane, Wharton's jelly and one or more umbilical cord vessels. In another embodiment, the umbilical cord or components thereof includes an isolated umbilical cord (e.g., comprising Wharton's jelly and vessels, Wharton's jelly only, or vessels only) that has been flattened into a sheet or strip. The umbilical cord or components thereof can be a substantially tubular structure from which the contents (Wharton's jelly and vessels) have been removed. The umbilical cord or components thereof can also include an umbilical cord membrane that has been slit or cut for part or all of the length of the umbilical cord to expose the contents of the umbilical cord.

In one embodiment, the umbilical cord is separated from the placenta after delivery of the newborn. The umbilical cord may be used immediately, or may be stored for several days from the time of delivery prior to any further treatment. The umbilical cord is separated from the placental disc, and is typically massaged to remove umbilical cord blood. Optionally, the umbilical cord is sectioned into pieces of about 8 cm to about 18 cm in length. The umbilical cord or umbilical cord sections can then be stored for up to about 72 hours in a sterile, preferably buffered, saline solution, such as 0.9% sterile NaCl solution. Preferably, the umbilical cord is stored under refrigeration, at a temperature of about 1-5° C.

The umbilical cord can be slit or cut longitudinally. This allows the umbilical cord membrane to be laid flat, allowing, e.g., removal of the Wharton's jelly, and/or one or more of the umbilical cord arteries or the umbilical cord can be further processed "as is", wherein the cord comprises the umbilical cord membrane, vessels, and Wharton's jelly.

In one embodiment, the umbilical cord biomaterial is substantially decellularized; that is, substantially all cellular material and cellular debris (e.g., all visible cellular material and cellular debris) can removed from the umbilical cord. Any decellularizing process known to one skilled in the art may be used.

In another embodiment, the umbilical cord or Wharton's jelly contains a significant amount of ECM components which include collagen, HA, and proteoglycans and stem cells. In some embodiments, the micronized Wharton's jelly further comprises growth factors, including fibroblast growth factor (FGF), insulin-like growth factor I (IGF-I), transforming growth factor beta (TGF-beta), platelet-derived growth factor (PDGF) and epidermal growth factor (EGF), etc.

In some embodiments, the multi-layered tissue graft includes from 1 to 10 wt %, 10 to 20 wt %, 20 to 30 wt %, 30 to 40 wt %, 40 to 50 wt %, 50 to 60 wt %, 60 to 70 wt %, 70 to 80 wt % umbilical cord biomaterial relative to the total weight of the multi-layered tissue graft. It should be understood that any subvalue or subrange from within the values described above, including endpoints, are contemplated for use with the embodiments described herein.

The Multi-Layered Tissue Grafts: Combining the Collagen Layers with the Layers Derived from Placental Components and/or the Umbilical Cord Components After individual layers of collagen and the layers from the placental tissue and/or the umbilical cord have been prepared, they can be combined into the disclosed multi-layer tissue grafts. Thus, in one aspect provided is a multi-layered tissue graft comprising a collagen layer and at least one separated and washed placental tissue component and/or umbilical cord component, wherein the collagen is human collagen substantially free of non-human antigens.

U.S. Pat. Nos. 8,357,403 and 8,323,701, incorporated herein by reference in their entireties, describe methods for making layered tissue grafts. By way of example only, tissue grafts may comprise a layer of amnion with epithelial cells optionally removed from the epithelial side whereupon a collagen layer is applied to the base amnion layer to produce the tissue graft. In a preferred embodiment, a layer of amnion with epithelial cells optionally removed from the epithelial side is placed on top of the graft with the epithelial side facing up. In some embodiments, the fibroblast layer of the amnion layer(s) acts as an adhesive for the next layer. Although in this aspect, the fibroblast layer is used to adhere the membranes together, other techniques and materials such as, for example, fibrin glue, gelatin, photochemical techniques, and suturing can be used to produce the laminated tissue graft. In one embodiment, the graft is not held together by sutures.

In some embodiments, the collagen layer is interposed between a first and a second layer of separated and washed placental tissue. In some embodiments, the placental tissue component derives from at least one amnion layer. In some embodiments, the placental tissue component is at least one chorion layer. In some embodiments, the collagen layer is interposed between a first and a second layer of separated and washed umbilical cord components.

Non-limiting examples of the multi-layer tissue grafts include layers of amnion/collagen/amnion; amnion/collagen/chorion; chorion/collagen/chorion; amnion/collagen/umbilical-cord; chorion/collagen/umbilical-cord; umbilical-cord/collagen/umbilical-cord; each of which may have one or more additional layers of amnion (with the fibroblast layer and/or the epithelial cells of the epithelial cellular layer intact or partially, substantially, or completely removed), chorion, a reconstituted collagen layer, an umbilical cord layer, Wharton's jelly and/or other umbilical cord components, biocompatible polymers or any combination thereof. The designation "amnion/collagen/amnion," for example, means that a layer of collagen is interposed between two layers of amnion. It is important to note that when multiple amnion layers are used, it is not necessary to partially remove the epithelial cells from the basement membrane for those layers that are not in direct contact with host cells.

In some embodiments of the multi-layer tissue grafts, the at least one amnion layer may comprise an epithelial side and a fibroblast side (fibroblast cellular side), wherein neither side has been partially or substantially decellularized. In other embodiments of the multi-layer tissue grafts, the at least one amnion layer may comprise an epithelial side and a fibroblast side, wherein the epithelial side has been partially or substantially decellularized, but the fibroblast side has not been partially or substantially decellularized. In still other embodiments of the multi-layer tissue grafts, the at least one amnion layer may comprise an epithelial side and a fibroblast side, wherein both the epithelial side and the fibroblast side have been partially or substantially decellularized.

In those multi-layer tissue grafts that include an amnion layer, such an amnion layer can be laid on a suitable drying fixture, where the epithelial side is adjacent to the surface of the drying fixture. In other aspects, the amnion can be placed on the surface of the drying fixture such that the epithelial side is facing up. In either case, a collagen layer can be laid on top of the amnion layer, followed by another amnion layer such that the collagen layer is sandwiched between amnion layers. In some embodiments, the collagen layer is sandwiched between amnion layers and the collagen layer contacts the epithelial side of each amnion layer.

The actual number and types of layers will depend upon the medical application and/or surgical need and procedure with which the tissue graft is designed to be used. Some applications may require a thicker or stronger tissue graft. In some embodiments, the laminated tissue graft comprises more than one layer of collagen. The collagen layers may be adjacent to one another or alternated with other biocompatible membranes. In some embodiments, all of the collagen layers are made of the same form of collagen. In some embodiments, different forms of collagen may be used for different layers. For example, one layer may be comprised of collagen fibers while another layer may be comprised of collagen gel. The collagen layer(s) may be of variable thickness, depending on the desired application.

In some aspects, the multi-layer tissue grafts, or micronized compositions below, comprise one or more biocompatible polymers. Preferred biocompatible polymers useful in this invention include biodegradable polymers. Suitable polymers include, without limitation, naturally-occurring polymers, synthetic polymers or mixtures thereof. Other examples of naturally-occurring biocompatible polymers include, but are not limited to, hyaluronic acid, fibrin, fibrous or globular proteins, complex carbohydrates, glycosaminoglycans, such as, or mixtures thereof. Thus, in one embodiment, the polymer may include elastin, laminin, hyaluronic acid, alginic acid, desmin, versican, fibrin, fibronectin, vitronectin, albumin, and the like. Exemplary synthetic biocompatible polymers include, but are not limited to, polyoxyalkylenes (e.g., polyoxyethylene, polyoxypropylene, copolymers of oxyethylene and oxypropylene, and the like), polyethylene glycol, polymethylene glycol, polytrimethylene glycols, polyvinylpyrrolidones, caprolactones, 2-hydroxyethyl methacrylate (HEMA), silicone such as Nusil MED-6215 or other silicone suitable for implantation, poly(epsilon-caprolactone) dimethylacrylate, polysulfone, (poly)methyl methacrylate (PMMA), soluble Teflon-AF, poly ethylene teraphthalate (PET, Dacron), Nylon, polyvinyl alcohol, polyurethane, hydroxyapatite, and the like and mixtures thereof. Such polymers preferably have an average molecular weight of at least about 10,000 and more preferably from about 10,000 to about 1,000,000. In some embodiments, these polymers preferably have an average molecular weight of at least 10,000 and more preferably from about 10,000 to about 100,000. The polymers described herein can be either cross-linked with non-chelating agents or non-cross-linked. Common non-chelating cross-linking agents include carbodimides, diisothiocyanates, dicarboxylic acids, diamines and the like.

All suitable polymers are biocompatible, and preferably non-toxic and non-inflammatory when administered in vivo, and will more preferably be degradable in vivo with a degradation time of at least several months.

A number of biodegradable, biologically compatible components can be added to the multi-layered tissue grafts. Examples of such materials include, but are not limited to amnion (with the fibroblast layer and/or the epithelial cells of the epithelial cellular layer intact or partially, substantially, or completely removed), chorion, a reconstituted collagen layer, an umbilical cord layer, Wharton's jelly and/or other umbilical cord components, biocompatible polymers or any combination thereof.

In some aspects, the multi-layered tissue grafts described herein are dehydrated. In some embodiments, the multi-layered tissue grafts are freeze-dried. In certain embodiments, the multi-layered tissue grafts described herein are dehydrated using a dehydration device as described in U.S. patent application Ser. No. 13/851,736, which modifies the drying apparatus as described in U.S. patent application Ser. No. 13/744,332, both applications which are incorporated herein by reference in their entireties.

In one embodiment, provided is a composition comprising a multi-layered tissue graft, where the tissue graft has been dehydrated to have a water content of less than 30%, 20%, 10% or 5%.

When completed, dehydrated processed tissue graft may have a semi-transparent appearance with a whitish coloration. The tissue is pliable to withstand bending and sizing in its dry, non-hydrated state. The tissue grafts described herein can be stored at room temperature for extended periods of time.

Optional Cross-Linking

Depending upon the application of the laminated tissue graft, one or more layers of the laminated tissue graft can be optionally fixed, i.e., cross-linked. In other words, each of the layers may be fortified by cross-linking with itself. Alternatively, one or more layers may be cross-linked together. Not wishing to be bound by theory, the cross-linking of the placental tissue can modify the resorption properties of the placental tissue. For example, the placental tissue can be cross-linked in order to regulate the rate of release of growth factors present in the placental tissue. In other aspects, the cross-linked placental tissue can be sufficiently cross-linked in order to prevent bioactive agents (e.g., INFUSE®) from leaching out of the tissue graft. Here, the cross-linked placental tissue acts as a barrier.

The collagen layer, placental tissue and/or umbilical cord layers can be cross-linked using a number of techniques. In one aspect, cross-linking may be achieved by chemical, thermal, radiation, fibronectin, fibrinogen and/or hydrogel cross-linking methods. In other aspects, the placental tissue can be individually treated with a cross-linking agent prior to lamination and formation of the tissue graft. In general, the cross-linking agent is nontoxic and non-immunogenic. When two or more placental tissues are treated with the cross-linking agent, the cross-linking agent can be the same or different. In one aspect, the layers of the tissue graft can be treated separately with a cross-linking agent or, in the alternative, the layers can be treated together with the same cross-linking agent. In certain aspects, the layers can be treated with two or more different cross-linking agents.

The conditions for crosslinking the collagen layer, placental tissue and/or umbilical cord layers can vary. In one aspect, the placental tissue or graft can be placed in a container holding an aqueous solution of the cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. In another aspect, the placental tissue or graft is treated with the cross-linking agent for 1 to 2 seconds up to 60 minutes. In a further aspect, the placental tissue or graft is treated with the cross-linking agent at room temperature up to 50° C.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the placental tissue to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof. Thus, in one aspect, the tissue graft includes at least one cross-linker covalently attached to one or more layers. In another aspect, a tissue graft includes a laminate, wherein the layers are covalently attached to one another via a cross-linker.

The cross-linking agent can be any suitable polymerizing (i.e., cross-linking) material, such as, but not limited to, the cross-linking agents described above, NDGA, 3,4-dihydroxyphenylalanine, dopamine, 3,4-dihydroxybenzaldehyde, 3,4-dihydroxybenzoic acid, carbodiimide, glutaraldehyde, formaldehyde, tannic acid, isocyanates, and epoxy resins. In other embodiments, the cross-linking agent can be any suitable polymerizing material in which at least one reactive group of the peptide is part of a diamino acid, such as but not limited to, lysine, arginine, asparagine, cysteine, glutamine, histidine and ornithine. In these aspects, hydroxyl groups and mercapto groups on the peptide may contribute to the cross-linking reaction. In other aspects, a dicarboxylic acid may be used as the cross-linking agent, thereby introducing a hydrocarbon bridge in-between the cross-linked sections having a free amino, hydroxyl or thiol group. In particular embodiments, the cross-linking agent comprises a quinone group and/or a catechol group. Exemplary cross-linking agents that can comprise a quinone and/or catechol functional group include, but are not limited to NDGA, 3,4-dihydroxyphenylalanine, and dopamine. Thus, the polymerized collagen can comprise one or more quinone and/or catechol groups.

Micronized Compositions

In one aspect, a micronized composition is provided, where the micronized composition include micronized collagen and one or both of micronized placental components and micronized umbilical cord components. "Micronization" is performed by mechanical grinding or shredding. The micronized composition can be prepared by combining the components either before or after micronization. For example, the micronized composition can be formed by separately micronizing collagen and one or both of the placental components and the umbilical cord components, followed by mixing the separately micronized components together. In other words, each of the collagen, placental components and/or umbilical cord components can be separately micronized before being combined. Alternatively, the collagen layer can be combined with a layer derived from placental components and/or a layer derived from umbilical cord components to form any of the multi-layered tissue grafts described herein before the multi-layered tissue graft is micronized.

As mentioned, the micronized composition may include micronized placenta tissue or a component thereof, such as micronized amnion, described in PCT Application No. PCT/US12/24798, as well as in U.S. provisional application Ser. Nos. 61/442,346, 61/543,995, and 61/683,700. The contents of these applications are specifically incorporated by reference in their entireties.

The micronization can be done using instruments known in the art. For example, the Retsch Oscillating Mill MM400 can be used to produce the micronized compositions described herein. In another aspect, micronization is performed by cryogenic grinding. In this aspect, the grinding jar containing the tissue is continually cooled with liquid nitrogen from the integrated cooling system before and during the grinding process. Thus, the sample is embrittled and volatile components are preserved. Moreover, the denaturing of proteins in the tissue is minimized or prevented. In one aspect, the CryoMill manufactured by Retsch can be used in this aspect.

For example, the collagen, placental components and/or umbilical cord components can be placed in 50 mL vials and the vials are subsequently sealed. The vials are placed in the Cryo-block, and the Cryo-block is placed in a Cryo-rack. The Cryo-rack is placed into a liquid nitrogen holding-Dewar flask. The tissue are subjected to vapor phase cooling for no more than 30-60 minutes. The Cryo-rack is removed from the Dewar flask, and the Cryo-block is removed from the Cryo-rack. The Cryo-block is placed into the Grinder (SPEX Sample Prep GenoGrinder 2010) and set at 1,500 rpm for 20 minutes. After 20 minutes has elapsed, the tissue is inspected to ensure micronization. If necessary, the tissue is placed back into the Dewar flask for an additional 30-60 minutes, and moved to the grinder for an additional 20 minutes to ensure sufficient micronization.

Separation of particle sizes can be achieved by fractionation of the micronized material in sterile water by forming a suspension of particles. The upper most portion of the suspension will contain predominantly the smallest particles and the lower most portion of the suspension will contain predominantly the heaviest particles. Fractionation leads to particle size separation and repeated fractionation will lead to separation of the micronized particles into varying sizes. The so separated particles can be recombined in the desired ratio of particle size as is most appropriate for an intended use.

In another embodiment, separation is done using sieves. For example, once the material is sufficiently micronized it is sorted using a series of American Standard ASTM sieves. In some embodiments, the sieves can be placed in the following order: 355 µm, 300 µm, 250 µm, 150 µm, and 125 µm. The micronized material is transferred from the 50 mL vials to the 355 µm sieve. Each sieve is agitated individually in order to thoroughly separate the micronized particles. Once the micronized particles are effectively separated using the sieves, the micronized particles having particle sizes of 355 µm, 300 µm, 250 µm, 150 µm, and 125 µm are collected in separate labeled vials.

The particle size of the micronized collagen, placental components and/or umbilical cord components can vary as well depending upon the application. It is to be understood that the term "micronized" is meant to include micron and sub-micron sized particles. In one aspect, the micronized Wharton's jelly has particles that are at or less than 500 µm, at or less than 400 µm, at or less than 300 µm, at or less than 200 µm, at or less than 100 µm, at or less than 75 µm, at or less than 50 µm, at or less than 25 µm, at or less than 20 µm, at or less than 15 µm, at or less than 10 µm, at or less than 9 µm, at or less than 8 µm, at or less than 7 µm, at or less than 6 µm, at or less than 5 µm, at or less than 4 µm, at or less than 3 µm, at or less than 2 µm, or from 2 µm to 400 µm, from 25 µm to 300 µm, from 25 µm to 200 µm, or from 25 µm to 150 µm. In one aspect, the micronized composition has particles that have a diameter less than 150 µm, less than 100 µm, or less than 50 µm. In other aspects, particles having a larger diameter (e.g. 150 µm to 350 µm) are desirable. In other aspects, the particles have a diameter of about 25 µm to about 75 µm. In all cases, the diameter of the particle is measured along its longest axis.

In some embodiments, the micronized collagen, placental components and/or umbilical cord components have a desired size distribution. For example, smaller sized particles may provide fast effect and larger particles can provide long term benefit. In some embodiments, about 50% of the micronized composition has a diameter of less than 40 μM, about 25% the micronized composition has a diameter of from 40 μM to less than 60 μM, and about 25% of the micronized composition has a diameter of more than 60 μM. In some embodiments, about 25% of the micronized composition has a diameter of less than 40 μM, about 25% the micronized composition has a diameter of from 40 μM to less than 60 μM, and about 50% of the micronized composition has a diameter of more than 60 μM.

In one embodiment, the surface area to volume ratio of the particles (based on a sphere having a range of diameters as described above) is between the range of about $0.06\ \mu m^{-1}$ to about $6\times10^4\ \mu m^{-1}$, about $0.06\ \mu m^{-1}$ to about $6\times10^3\ \mu m^{-1}$, about $0.06\ \mu m^{-1}$ to about $6\times10^2\ \mu m^{-1}$, or about $0.6\ \mu m^{-1}$ to about $6\times10^2\ \mu m^{-1}$.

In one aspect, a filler can be added to the micronized composition before or after micronization. Examples of fillers include, but are not limited to, allograft pericardium, allograft acellular dermis, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added to the micronized composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the micronized composition with bioactive agent to the region of interest, the bioactive agent is delivered to the region over time. Thus, the micronized particles or a composition thereof described herein are useful as delivery devices of bioactive agents and other pharmaceutical agents when administered to a subject. Release profiles can be modified based on, among other things, the selection of the components used to make the micronized compositions as well as the size of the particles.

In other aspects, the micronized compositions described herein can be formulated in any pharmaceutically acceptable excipients to form a suspension or a gelatinous gel composition. The composition can be a liquid, gel, or paste. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

In some embodiments, sterile water is used to create a flowable gel composition from the micronized collagen and one or both of micronized placental components and micronized umbilical cord components. For example, about 0.1 to about 1 g (such as about 0.5 g) of micronized collagen and one or both of micronized placental components and micronized umbilical cord components can be mixed with about 1 mL to about 2 mL (such as about 1.3-1.4 mL) of water to provide a flowable gel material. In some embodiments, the concentration of the micronized collagen and one or both of micronized placental components and micronized umbilical cord components in the composition is about 0.05 g/mL to about 1 g/mL, such as about 0.05 g/mL, about 0.1 g/mL, about 0.2 g/mL, about 0.3 g/mL, about 0.4 g/mL, about 0.5 g/mL, about 0.6 g/mL, about 0.7 g/mL, about 0.8 g/mL, about 0.9 g/mL, about 1 g/mL, or any ranges between any two values, including the end points. The material is in a smooth consistency that is able to be loaded to a syringe and pass through a needle, such as a 25-27 gauge needle.

In some embodiments, droplets of the above gel are applied onto a surface, such as a smooth and non-embossed surface of a board, and allowed to dry substantially or completely. In some embodiments, the diameter of droplets are about 5 to about 1 mm, such as about 2.5 mm. After drying, solid pellets form with minimum reduction in overall diameter. In some embodiments, the solid pellets are in a circular shape/configuration. As used herein, substantially means that the dried pellets comprises no more than 10%, 5%, 2%, 1%, 0.5% or 0.1% residue water.

The pellets can be placed in sterile water or other aqueous solution (e.g., saline) to re-hydrate. In some embodiments the re-hydration time is about or more than 1 hour. In some embodiments, the diameter of the pellets increases after rehydration. In some embodiments, the diameter increases by about 1.1 to 3 fold, such as about 1.5 to 2.5 fold or about 2 fold. In some embodiments, there is no indication of loss of integrity in size or shape in aqueous condition for an extended period, such as more than 24 hours.

In some embodiments, the micronized collagen and one or both of micronized placental components and micronized umbilical cord components are compressed into a mold having a desired shape or size to form a molded micronized composition that takes the shape and size of the mold and exhibits a desired cohesiveness and density. It is within the purview of one of ordinary skill in the art to select suitable molding material, such as silicone, resin, Teflon®, or stainless steel, to form a mold of desired shape and size.

The micronized compositions described herein can be administered in a number of ways depending on whether local or systemic treatment is desired, and on the area to be treated. In one aspect, administration can be by injection, where the composition is formulated into a liquid or gel. In other aspects, the composition can be formulated to be applied internally to a subject. In other aspects, the composition can be applied topically (including ophthalmically, vaginally, rectally, intranasally, orally, or directly to the skin).

In one aspect, the micronized compositions can be formulated as a topical composition applied directly to the skin. Formulations for topical administration can include, without limitation, emulsions, creams, aqueous solutions, oils, ointments, pastes, gels, lotions, milks, foams, suspensions and powders. In one aspect, the topical composition can include one or more surfactants and/or emulsifiers. Topical application of micronized particles is particularly well suited for the treatment of burns, psoriatic sores, dermatitis, wrinkles, and the like.

Methods of Treatment

In another aspect of this invention, a method for treating a subject is disclosed, the method comprising contacting the subject with any of the disclosed multi-layered tissue grafts or micronized pharmaceutical compositions.

In one aspect, the grafts or micronized pharmaceutical compositions described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

In a further aspect, the present invention provides methods of using the collagen-containing multi-layered tissue grafts or micronized pharmaceutical compositions of the invention therapeutically, prophylactically or cosmetically. The collagen-containing multi-layered tissue grafts of the present invention have a broad array of potential uses that include, but are not limited to, manufacture of engineered tissue and organs, including structures such as patches or plugs of tissues or matrix material, prosthetics, and other implants, tissue scaffolding, repair or dressing of wounds, hemostatic devices, devices for use in tissue repair and support such as sutures, natural coatings or components for synthetic implants, cosmetic implants and supports, repair or structural support for organs or tissues, substance delivery, bioengineering platforms, platforms for testing the effect of substances upon cells, cell culture, and numerous other uses.

In another aspect, the tissue grafts or micronized pharmaceutical compositions are useful in dental applications. For example, the grafts or micronized pharmaceutical compositions can be used around dental implants or in the treatment of advanced gingival recession defect. In another aspect, the grafts can be used in guided tissue regeneration.

In other aspects, the grafts or micronized pharmaceutical compositions described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts or micronized pharmaceutical compositions described herein can be used to wrap tendon repairs to prevent scar formation on the healing tendon. They can also provide a protective, enclosed environment for the repair to progress successfully. The tissue or micronized pharmaceutical compositions grafts can be used as an off-the-shelf tendon and ligament to replace the need to purchase an allograft or perform tendon or ligament transfer.

In other aspects, the tissue grafts or micronized pharmaceutical compositions described herein can be used in the reinforcement of rotator cuffs. Some rotator cuff tears are large enough that they require a reinforcement matrix to support the repair due to lack of viable native tissue. The tissue grafts or micronized pharmaceutical compositions described herein can be used as a matrix to reinforce a repair. In one aspect, the tissue grafts described herein can be used to repair knee cartilage. For example, the tissue grafts or micronized pharmaceutical compositions can be used as a barrier to hold cell cultured chondrocytes or other pro-cartilage regeneration matrix inside a chondral defect. In this aspect, the tissue graft or micronized pharmaceutical compositions would be utilized as a flap to close the defect and hold the matrix in place.

In one aspect, the tissue grafts or micronized pharmaceutical compositions can be used to repair peripheral nerves. The tissue graft or micronized pharmaceutical compositions can be used as a wrap on nerve repairs to prevent scar formation onto the healing nerve. The tissue graft can also provide a protective enclosed environment for the repair to progress successfully. In other aspects, the tissue grafts or micronized pharmaceutical compositions can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts or micronized pharmaceutical compositions can be laid on the nerves to keep them from scarring and possibly damaging the nerves.

In other aspects, the tissue grafts or micronized pharmaceutical compositions described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In another aspect, the tissue grafts or micronized pharmaceutical compositions can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laparoscopic approach.

The tissue grafts or micronized pharmaceutical compositions can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts or micronized pharmaceutical compositions can be used to reline the uterine wall after severe endometriosis treatments and increase the patient's ability to conceive. In a further aspect, the tissue graft or micronized pharmaceutical compositions can be used as an anti-adhesion barrier after removal of ovarian cyst or aid in the repair of vaginal wall erosion.

In other aspects, the tissue grafts or micronized pharmaceutical compositions can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts or micronized pharmaceutical compositions described herein can be used as a patch to support the repair of vascular and cardiac defects caused by operations and complications such as carotid artery repair, coronary artery bypass grafting, congenital heart disease, heart valve repair, and vascular repair (i.e. peripheral vessels). In other aspects, the tissue graft or micronized pharmaceutical compositions can be configured into a stent.

The tissue grafts or micronized pharmaceutical compositions described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts or micronized pharmaceutical compositions can be used to facilitate closure of anastomosis, an anti-adhesion barrier for anastomosis, or an anti-adhesion barrier for hernia repair.

In other aspects, the tissue grafts or micronized pharmaceutical compositions can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts or micronized pharmaceutical compositions described herein can be used to prevent the additional trauma associated with harvesting the patients' own tissue and save time in surgery. In other aspects, the tissue grafts or micronized pharmaceutical compositions can be used as a wound covering after adenoidectomy, a wound cover after tonsillectomy, or facilitate repair of the Schneiderian membrane.

In other aspects, the tissue grafts or micronized pharmaceutical compositions described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts or micronized pharmaceutical compositions described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts or micronized pharmaceutical compositions can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the tissue grafts or micronized pharmaceutical compositions can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

In another aspect, the tissue grafts or micronized pharmaceutical compositions can be used in the treatment of bone defects and bone repair. In one aspect, the tissue grafts can be used in dental surgery to provide primary stability in mandibular and maxillary horizontal and or vertical guided bone regeneration, repair of dental implants, repair of the sinus, and over mandibular block graft donor sites. In other aspects, the tissue grafts or micronized pharmaceutical compositions can be used in craniofacial surgery, including but not limited to treatment of bony defects caused from trauma, surgically created bone defects such as burrholes and trephine defects, zygomatic defects, and orbital defects. In orthopedic surgery, the tissue grafts or micronized pharmaceutical compositions can be used to treat bone defects including but not limited to open and closed fractures, segmental defects, osteochondral defects, spinal fusion, and other non-load bearing regeneration procedures. In other aspects, the tissue grafts or micronized pharmaceutical compositions can be used in the treatment of a segmental long bone defect.

Depending upon the application of the graft, the graft or micronized pharmaceutical compositions can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, the micronized pharmaceutical compositions or one or more membrane layers of the tissue graft absorb the bioactive agent. Upon application of the wet tissue graft with bioactive agent to the wound, the bioactive agent is delivered to the wound over time.

Although the tissue grafts or micronized pharmaceutical compositions described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

The micronized tissue grafts or micronized pharmaceutical compositions described herein are useful in a variety of cosmetic treatments including, but not limited to, remodeling, filling or reconstruction of soft tissues, the treatment of wrinkles, creases and scars, burns, ulcers, soft tissue augmentation, facial lipoatrophy, as an analgesic and anti-inflammatory. This discussion of possible uses is not intended to be exhaustive and many other embodiments exist.

In one aspect, the tissue grafts or micronized pharmaceutical compositions can be used as dermal fillers. The skin is made up of three layers: the epidermis, dermis, and subcutaneous. The epidermis is the outer layer and functions as a barrier to the external environment. The dermis is the second layer of the skin containing the structural elements, which are collagen and elastin fibers. The collagen gives the skin its strength while the elastin fibers give the skin its elasticity. In between the epidermis and dermis is an area termed the dermal-epidermal junction. It interlocks forming fingerlike projections, called rete ridges, increasing the surface area of the epidermis that is exposed to the blood vessels in the dermis. The cells of the epidermis receive its nutrients from the blood vessels in the dermis. The last layer of skin is the subcutaneous tissue which contains the fat cells. These fat cells make the skin look plump and youthful. It also provides insulation to the body.

As a person ages, the skin goes through many changes that will eventually lead to wrinkles. The number of epidermal cells decreases causing the skin to look noticeable thinner and making it more difficult for the skin to repair itself. The dermal layer not only gets thinner, but also produces less collagen and the elastin fibers wear out causing a decrease in elasticity. These changes in the scaffolding of the skin cause the skin to wrinkle and sag. The rete-ridges of the dermal-epidermal junction flatten out, making the skin more fragile and easier for the skin to shear. The flattened rete-ridges decrease the surface area of epidermis in contact with the dermis, which leads to a decrease in the amount of nutrients available to the epidermis. This also interferes with the skin's normal repair process. In the subcutaneous layer, the fat cells get smaller with age leading to more noticeable wrinkles and sagging.

Amnion contains growth factors such as EGF, bFGF, and PDGF that promote wound healing and re-epithelialization. Not wishing to be bound by theory, the application of a topical composition composed of the tissue grafts or micronized compositions described herein where the epithelial layer of the skin is disrupted can be effective in delivering the growth factors directly to the injured site to promote healing. Amnion is a unique ECM due to the presence of collagen types IV, V and VII, which enables the amnion to bind water and swell.

Similarly, the intermediate tissue layer of the amniotic membrane is composed largely of glycoproteins and proteoglycans, which also enables the intermediate tissue layer to bind water. Thus, the tissue grafts or micronized compositions when applied to the skin or wound help retain water in the skin, which facilitates wound healing. Another important component in the tissue grafts or micronized compositions that is beneficial to skin is proteoglycans. As discussed above, proteoglycans allow the intermediate tissue layer to bind water to such a large degree and swell considerably. As noted before, the fat cells in the subcutaneous layer get smaller with age leading to more noticeable wrinkles Thus, by injecting a dermal filler composed of the tissue grafts or micronized compositions described herein can make the skin look more noticeably plump and youthful.

In one embodiment, a multi-layer tissue graft of the invention, preferably micronized, may also be used to augment creased or sunken areas of the face and/or to add or increase the fullness to areas of the face and body of a patient. The areas of the face and/or body requiring augmentation may be the result of, e.g., aging, trauma, disease, sickness, environmental factors, weight loss, child birth, or a combination thereof. Non-limiting examples of an area of the face or body of a patient where a tissue graft of the invention may be injected or otherwise administered include the undereye, temple, upper malar, sub malar, chin, lip, jawline, forehead, glabella, outer brow, cheek, area between upper lip and nose, nose (such as the bridge of the nose), neck, buttocks, hips, sternum, or any other part of the face or body, or a combination thereof.

In further aspects, a multi-layer tissue graft of the invention, preferably micronized, may be used to treat skin deficiencies including, but not limited to, wrinkles, depressions or other creases (e.g., frown lines, worry lines, crow's feet, marionette lines), stretch marks, internal and external scars (such as scars resulting from injury, wounds, accidents, bites, or surgery), or combinations thereof. In some embodiments, a tissue graft of the invention may be used for the correction of, for example, "hollow" eyes, visible vessels resulting in dark circles, as well as visible tear troughs. A tissue graft as described herein may also be used, for example, for correction of the undereye after aggressive removal of undereye fat pads from lower blepharoplasty or correction of the lower cheek after aggressive buccal fat extraction or natural loss. In one embodiment, a tissue graft of the invention may be used to correct the results of rhinoplasty, skin graft or other surgically-induced irregularities, such as indentations resulting from liposuction. In other embodiments, a tissue graft of the invention may be used for the correction of facial or body scars (e.g., wound, chicken pox, or acne scars). In some embodiments, a tissue graft of the invention is injected or otherwise administered into a patient for facial reshaping. Facial reshaping using the methods of the invention may be completed in a patient with neck laxity, or having a gaunt face, long face, bottom-heavy face, asymmetrical face, a chubby face, or having a face with localized fat atrophy, a midface retrusion, sunken eyes, and/or any combinations thereof.

In one embodiment, the methods of the invention comprise injecting or otherwise administering a tissue graft or micronized pharmaceutical composition of the invention to a patient for the treatment of a perceived skin deficiency, such as skin deficiency caused by a disease or illness, such as cancer or acne. The deficiency can be the direct or indirect result of the disease or illness. For example, a skin deficiency can be caused by a disease or illness or can be caused by a treatment of a disease or illness.

Example 1—Preparation of the Reconstituted Collagen

The collagen is obtained and purified from human placental tissue using standard procedures. For example, the collagen can be obtained from placental tissue by mincing and extracting the tissue with aqueous acid (e.g., 3% acetic acid, pH 2.5) for 2-24 hours at 25-50° C. The acid extracted collagen can be separated from the insoluble tissue residues by centrifugation. The residue is digested with pepsin in aqueous acid (e.g., 3% acetic acid, pH 2.5) for 2-24 hours at 25-50° C. The digest is centrifuged (e.g., at 37,000 g for 2-60 min.) The supernatant is collected and NaCl is added (e.g., to about 0.7 m) while stirring on ice. The resulting precipitate is collected by centrifugation as above, and then redissolved acid (e.g., 3% acetic acid, pH 2.5). NaCl was again added to (e.g., to about 0.7 m) and the precipitate is collected by centrifugation. The purified collagen is redissolved in acid (e.g., 3% acetic acid, pH 2.5) and stored at 25-50° C. The purity of the collagen can be assessed by SDS/PAGE using 4-20% linear gradient Tris-glycine gels. The purified collagen can optionally be fixed (i.e., crosslinked) and added as a gel to the multilayered tissue grafts or the purified collagen can optionally be fixed and made into layers that are dried into sheets before being added to the multilayered tissue grafts.

Example 2—Preparation of Crosslinked Collagen Fibers

Fibers are prepared by dialyzing 10 ml of the purified collagen in 0.32 ml/cm dialysis tubing against water, and then dialyzing against 30 mm $NaH_2PO_4$, 140 mm NaCl pH 7.4 (PBS) at 37° C. overnight. The collagen fiber gel is extruded into a water bath, clamped at one end, and hung vertically in air to dry at room temperature. Dried fibers are hydrated in 0.1 m $NaH_2PO_4$, 0.15M NaCl pH 7.0 (PBS) for 30 min. Fibers are then treated with NDGA in PBS. NDGA is suspended in 1N NaOH. Solubilization of NDGA at concentrations greater than 10 mg/ml requires an addition of 10 ml 10n NaOH. 1 ml of the NDGA solution is added to the phosphate buffer in which the fibers are suspended. The fibers are agitated in the NDGA solutions for 24 h. The fibers are removed, briefly rinsed with water and hung vertically to dry. By washing the NDGA treated fibers with ethanol, unreacted NDGA contaminants are effectively removed. For the experiments reported here, all fibers are washed with 70% ethanol for at least 6 h, followed by extensive washing with PBS for 18 h at room temperature.

Example 3—Preparation of an Amnion Layer

Placenta is removed from the sterile shipment bag and transferred aseptically to a sterile processing basin within the critical environment. The sterile basin contains, preferably, 18% NaCl (hyperisotonic saline) solution that is at room or near room temperature. The placenta is gently massaged to help separate blood clots and to allow the placenta tissue to reach room temperature, which will make the separation of the amnion and chorion layers from each other, as discussed hereinafter, easier. After having warmed up to the ambient temperature (after about 10-30 minutes), the placenta is then removed from the sterile processing basin and laid flat on a processing tray.

Next, the amnion and chorion layers of the placenta tissue are then carefully separated. The materials and equipment used in this procedure include the processing tray, 18% saline solution, sterile 4×4 sponges, and two sterile Nalgene jars. The placenta tissue is then closely examined to find an area (typically a corner) in which the amniotic membrane layer can be separated from the chorion layer. The amniotic membrane appears as a thin, opaque layer on the chorion.

With the placenta tissue in the processing tray with the amniotic membrane layer facing down, the chorion layer is gently lifted off the amniotic membrane layer in a slow, continuous motion, using care to prevent tearing of the amniotic membrane. If the chorion layer is not needed, it may be gently scrubbed away from the amniotic membrane layer with one of the sterile 4×4 sponges by gently scrubbing the chorion in one direction. If the chorion is to be retained, then the separation process continues by hand, without the use of the sponges, being careful not to tear either the amnion layer or the chorion layer.

Care is then taken to remove blood clots and other extraneous tissue from each layer of tissue until the amniotic membrane tissue and the chorion are clean and ready for further processing. More specifically, the amnion and chorion tissues are placed on the processing tray and blood clots are carefully removed using a blunt instrument, a finger, or a sterile non-particulating gauze, by gently rubbing the blood until it is free from the stromal tissue of the amnion and from the trophoblast tissue of the chorion. The stromal layer of the amnion is the side of the amniotic membrane that faces the mother. In contrast, the basement membrane layer is the side of the amnion that faces the baby.

Using a blunt instrument, a cell scraper or sterile gauze, any residual debris or contamination is also removed. This step must be done with adequate care, again, so as not to tear the amnion or chorion tissues. The cleaning of the amnion is complete once the amnion tissue is smooth and opaque-white in appearance. If the amnion tissue is cleaned too much, the opaque layer can be removed.

Example 4—Preparation of a Multilayered Skin Graft

The cleaned amnion tissue (4 cm×3 cm) described above is set on a clean processing tray. A purified sheet (4 cm×3 cm) of NDGA-treated collagen fibers, as described above, are added to the amnion tissue on the side that previously contacted the chorion tissue. A second amnion tissue (4 cm×3 cm) is layered on top of the collagen sheet so that the collagen likewise contacts the second amnion tissue on the side that previously contacted the chorion tissue. The resulting multilayered skin graft having amnion/collagen/amnion is allowed to dry.

Example 5—Preparation of Micronized Compositions

The dried amnion/collagen/amnion tissue graft of the previous example is used to produce micronized particles according to the micronization process described in U.S. 2008/0046095, which is incorporated by reference in its entirety. Amnion/collagen/amnion tissue grafts (4 cm×3 cm) and two 9.5 mm steel grinding balls are placed in 50 mL vials and the vials subsequently sealed. The vials are placed in the Cryo-block, and the Cryo-block is placed in a Cryo-rack. The Cryo-rack is placed into a liquid nitrogen holding Dewar. Tissue samples are subjected to vapor phase cooling for 30-60 minutes. The Cryo-rack is removed from the Dewar, and the Cryo-block is removed from the Cryo-rack. The Cryo-block is placed into the Grinder (SPEX Sample Prep GenoGrinder 2010) and set at 1,500 rpm for 20 minutes. After 20 minutes has elapsed, the tissue is inspected to ensure micronization. If necessary, the tissue can be placed back into the Dewar for an additional 30-60 minutes, and moved to the grinder for an additional 20 minutes to ensure sufficient micronization. Once the tissue is sufficiently micronized it is sorted using a series of American Standard ASTM sieves. The sieves can be placed in the following order: 355 μm, 300 μm, 250 μm, 150 μm, and 125 μm. The micronized material is transferred from the 50 mL vials to the 355 μm sieve. Each sieve is agitated individually in order to thoroughly separate the micronized particles. Once the micronized particles are effectively separated using the sieves, the micronized particles having particle sizes of 355 μm, 300 μm, 250 μm, 150 μm, and 125 μm are collected in separate vials.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A multi-layered tissue graft comprising a collagen layer and at least one separated and washed placental tissue layer derived from at least one amnion layer, wherein the at least one separated and washed placental tissue layer comprises a basement membrane and a compact layer, and wherein the collagen layer is reconstituted human collagen substantially free of immunogenic agents.

2. The multi-layered tissue graft of claim 1, comprising a collagen layer interposed between the at least one separated and washed placental tissue layer and a second separated and washed placental tissue layer and/or umbilical cord component.

3. The multi-layered tissue graft of claim 1, wherein the collagen layer is at least 10 wt. % relative to the total weight % of the tissue graft.

4. The multi-layered tissue graft of claim 1, wherein the layers are laminated together.

5. The multi-layered tissue graft of claim 1, wherein the collagen layer is crosslinked.

6. The multi-layered tissue graft of claim 1, wherein the collagen layer has a tensile strength of at least about 100 kilopascals.

7. The multi-layered tissue graft of claim 6, wherein the collagen layer has a tensile strength of between about 500 kilopascals to about 10 megapascals.

8. The multi-layered tissue graft of claim 1, wherein the collagen layer has a stiffness of at least about 50 megapascals.

9. The multi-layered tissue graft of claim 8, wherein the collagen layer has a stiffness of between about 100 megapascals and about 500 megapascals.

* * * * *